United States Patent [19]
Saltzstein et al.

[11] Patent Number: 5,931,791
[45] Date of Patent: Aug. 3, 1999

[54] MEDICAL PATIENT VITAL SIGNS-MONITORING APPARATUS

[75] Inventors: William E. Saltzstein, Amity; Mohamed Sabri; Anthony P. Dobaj, both of Beaverton; Eric O. Baumann, Cornelius, all of Oreg.

[73] Assignee: Instromedix, Inc., Hillsboro, Oreg.

[21] Appl. No.: 08/964,111

[22] Filed: Nov. 5, 1997

[51] Int. Cl.$^6$ .................................................. A61B 5/02
[52] U.S. Cl. ............................................ 600/513; 128/904
[58] Field of Search .............................. 600/513; 128/904

[56] References Cited

U.S. PATENT DOCUMENTS

| | | |
|---|---|---|
| 3,886,314 | 5/1975 | Pori . |
| 3,938,507 | 2/1976 | Sarnoff et al. . |
| 3,971,980 | 7/1976 | Jungfer et al. . |
| 3,972,320 | 8/1976 | Kalman . |
| 4,108,166 | 8/1978 | Schmid . |
| 4,120,294 | 10/1978 | Wolfe . |
| 4,129,125 | 12/1978 | Lester et al. . |
| 4,173,971 | 11/1979 | Karz . |

(List continued on next page.)

FOREIGN PATENT DOCUMENTS

| | | |
|---|---|---|
| 0122888A2 | 10/1984 | European Pat. Off. . |
| 0645710A2 | 7/1994 | European Pat. Off. . |
| 0656718A2 | 6/1995 | European Pat. Off. . |
| 0645710A3 | 11/1995 | European Pat. Off. . |
| 81 19650 | 4/1983 | France . |
| 2845-679 | 4/1980 | Germany . |
| 27 53 165 | 6/1980 | Germany . |
| 8805282 | 7/1988 | WIPO ................................. 600/513 |

OTHER PUBLICATIONS

Comparison of Duplex and Triplex Memory Reliability, pp. 503–507, IEEE Transactions on Computers, vol. 45. No. 4., Apr. 1996.

*Symposium on the Engineering of Computer–Based Medical Systems*, pp. 22–27, Jun. 8–10, 1998.

English language abstract of published European Patent Application No. 645,710A2, Derwent Info. Ltd.

Fisher, Anne B., *House Calls*, Inc., pp. 72–79, Jul. 1989.

James E. McKee, Noel E. Evans and Frank J. Owens, A Simultaneous Full–Duplex Speech and Electrocardiogram Communications System, Proceedings of the Annual International Conference of the IEEE Engineering in Medicine and Biology Society, Baltimore, Nov. 3–6, 1994, vol. 16, pp. 902–903.

William Stallings, *Data and Computer Communications*, 2d. Ed., pp. 103–113, MacMillan Publishing Co., 1988.

Bernard L. Segal et al., Telephone Phonocardiograph, *The American Journal of Medical Electronics*, pp. 189–191, Jul.–Sep., 1964.

Kathy Brock, Inventors of Heart Monitor Tick Toward Prosperity, *The Business Journal*, p. 15, Sep. 17, 1990.

*Primary Examiner*—William E. Kamm
*Assistant Examiner*—Carl H. Layno
*Attorney, Agent, or Firm*—Klarquist, Sparkman, Campbell, Leigh and Whinston, LLP

[57] ABSTRACT

A portable multiple-vital signs monitor unit of the described apparatus is of ultra-light weight, e.g. less than one pound. In its preferred embodiment, the portable unit takes the form of a right parallelepiped enclosure the volume of which is only approximately 40 in$^3$ having operator display and control panels and body lead jacks on its face and periphery, respectively, and providing wireless remote full-function communication with an in situ base unit with which the portable monitor may optionally be docked. The base unit communicates via a single telephone line with a remote, typically central location including a host computer and a health care provider, preferably via concurrent voice and data transmission. In its preferred embodiment, the invented apparatus includes in the portable unit the capability for diagnostic quality ECG and pulse oximetry monitoring and in its base unit the capability diagnostic quality blood pressure monitoring.

23 Claims, 7 Drawing Sheets

U.S. PATENT DOCUMENTS

| | | |
|---|---|---|
| 4,216,462 | 8/1980 | McGrath et al. . |
| 4,230,127 | 10/1980 | Larson . |
| 4,256,117 | 3/1981 | Perica et al. . |
| 4,409,983 | 10/1983 | Albert . |
| 4,425,921 | 1/1984 | Fujisaki et al. . |
| 4,450,843 | 5/1984 | Barney et al. . |
| 4,494,553 | 1/1985 | Sciarra et al. . |
| 4,531,527 | 7/1985 | Reinhold, Jr. et al. . |
| 4,602,637 | 7/1986 | Elmqvist et al. . |
| 4,603,704 | 8/1986 | Mund et al. . |
| 4,611,604 | 9/1986 | Botvidsson et al. . |
| 4,679,000 | 7/1987 | Clark . |
| 4,715,381 | 12/1987 | Moberg . |
| 4,784,162 | 11/1988 | Ricks et al. . |
| 4,791,933 | 12/1988 | Asai et al. . |
| 4,799,491 | 1/1989 | Eckerle . |
| 4,802,488 | 2/1989 | Eckerle . |
| 4,803,625 | 2/1989 | Fu et al. . |
| 4,838,275 | 6/1989 | Lee . |
| 4,883,064 | 11/1989 | Olson et al. . |
| 4,928,690 | 5/1990 | Heilman et al. . |
| 4,933,873 | 6/1990 | Kaufman et al. . |
| 4,938,228 | 7/1990 | Righter et al. . |
| 4,945,477 | 7/1990 | Edwards . |
| 4,949,046 | 8/1990 | Seyfang . |
| 4,952,862 | 8/1990 | Biagetti et al. . |
| 4,958,641 | 9/1990 | Digby et al. . |
| 4,967,756 | 11/1990 | Hewitt . |
| 4,974,607 | 12/1990 | Miwa . |
| 4,979,235 | 12/1990 | Rumbaugh et al. . |
| 5,001,484 | 3/1991 | Weiss . |
| 5,007,429 | 4/1991 | Treatch et al. . |
| 5,012,814 | 5/1991 | Mills et al. . |
| 5,024,225 | 6/1991 | Fang . |
| 5,025,794 | 6/1991 | Albert et al. . |
| 5,033,474 | 7/1991 | Varelis et al. . |
| 5,036,513 | 7/1991 | Greenblatt . |
| 5,038,800 | 8/1991 | Oba . |
| 5,128,552 | 7/1992 | Fang et al. . |
| 5,142,484 | 8/1992 | Kaufman et al. . |
| 5,154,183 | 10/1992 | Kreyenhagen et al. . |
| 5,185,861 | 2/1993 | Valencia . |
| 5,191,891 | 3/1993 | Righter . |
| 5,216,596 | 6/1993 | Weinstein . |
| 5,226,431 | 7/1993 | Bible et al. . |
| 5,317,269 | 5/1994 | Mills et al. . |
| 5,321,618 | 6/1994 | Gessman . |
| 5,333,616 | 8/1994 | Mills et al. . |
| 5,339,823 | 8/1994 | Reinhold, Jr. . |
| 5,343,869 | 9/1994 | Pross et al. . |
| 5,351,695 | 10/1994 | Mills et al. . |
| 5,357,427 | 10/1994 | Langen et al. . |
| 5,365,935 | 11/1994 | Righter et al. . |
| 5,381,798 | 1/1995 | Burrows . |
| 5,390,238 | 2/1995 | Kirk et al. . |
| 5,394,882 | 3/1995 | Mawhinney . |
| 5,462,051 | 10/1995 | Oka et al. . |
| 5,465,727 | 11/1995 | Reinhold, Jr. . |
| 5,467,773 | 11/1995 | Bergelson et al. . |
| 5,474,090 | 12/1995 | Begun et al. . |
| 5,544,661 | 8/1996 | Davis et al. . |
| 5,553,609 | 9/1996 | Chen et al. . |
| 5,557,800 | 9/1996 | Kasimov et al. . |
| 5,607,454 | 3/1997 | Cameron et al. . |
| 5,613,495 | 3/1997 | Mills et al. . |
| 5,623,925 | 4/1997 | Swenson et al. . |
| 5,685,314 | 11/1997 | Geheb et al. . |
| 5,701,894 | 12/1997 | Cherry et al. ............................ 128/904 |
| 5,704,364 | 1/1998 | Saltzstein et al. . |

MEDICAL PATIENT VITAL SIGNS-MONITORING APPARATUS

TECHNICAL FIELD

The present invention relates generally to vital signs-monitoring apparatus. More particularly, it concerns apparatus including a portable, diagnostic-quality, multiple vital signs medical patient unit of extremely low mass that is easily transported by an ambulatory patient or nurse practitioner in a home or patient care facility and that is conveniently docked in a relatively fixed base unit.

BACKGROUND ART

Conventionally, multiple vital signs monitors are installed and used at fixed locations, bedside, in clinics and hospitals. They typically are not battery-operated, requiring instead power and input/output (I/O) cords and cables, and are made to be affixed to a bedside or other bedside equipment. Often, such multiple vital signs monitors are bulky, e.g. weighing up to one hundred pounds, and thus are impossible or at least very difficult to transport more than a few feet by hospital staff or contractors.

Conventional single vital sign monitors may be portable and relatively lightweight, but provide limited versatility, permitting the monitoring of only one patient vital sign, e.g. ECG (e.g. as measured by skin-contact, resistance-measuring electrodes) or blood pressure (preferably non-invasive BP—e.g. as measured by an inflatable, limb-encircling, artery-occluding pressure cuff) or blood-oxygen level (e.g. as measured by pulse oximetry or $SpO_2$), which it will be appreciated by those of skill in the art require relatively low bandwidths to provide diagnostic quality data. Known portable ECG monitors support only three-lead ECG monitoring, which is less reliable than twelve-lead monitoring. Some single vital sign monitors provide for real-time telemetry to a remote location of such monitored data, but do not provide for local, integral storage of such vital sign data for later outplay. By real time, it will be appreciated that minimization of the time delay between the talking of a patient vital sign measurement and the receipt thereof in usable form at a remote site by a physician or diagnostic technician is needed for high-quality patient care, and that such delay or latency preferably is on the order of a second, and preferably far less, and is no more than a very few seconds.

U.S. Pat. No. 5,333,616 entitled WRIST-WORN ECG MONITOR describes such a portable ECG monitor; U.S. Pat. No. 4,967,756 entitled BLOOD PRESSURE AND HEART RATE MONITORING METHOD AND APPARATUS describes such a BP monitor; and co-pending U.S. patent application Ser. No. 08/556,468 entitled CONCURRENT MEDICAL PATIENT DATA AND VOICE COMMUNICATION METHOD AND APPARATUS, issued Jan. 6, 1998, as U.S. Pat. No. 5,704,364, describes tele-monitoring over the public switched telephone network (PSTN). All are commonly owned herewith, and the disclosures of these patents and this application are incorporated herein by this reference.

DISCLOSURE OF THE INVENTION

Briefly, the portable multiple-vital signs monitor unit of the invented apparatus is designed and constructed to be ultra-light weight, e.g. less than one pound, yet without compromising utility and versatility in real-time, remote, medical patient diagnostic and prescriptive care. In its preferred embodiment, the portable unit takes the form of a right parallelepiped enclosure the volume of which is only approximately 40 $in^3$. The battery-operated, portable unit preferably includes operator display and control panels and body lead jacks on its face and periphery, respectively, and provides remote fill-function communication with an in situ base unit with which the portable monitor may optionally be docked. The base unit communicates via a single switched telephone line with a remote, typically central, location including a host computer and a health care provider, preferably via concurrent (or at least synchronized, e.g. time-stamped) voice and data transmission.

In its preferred embodiment, the invented apparatus includes the capability for diagnostic quality ECG and pulse oximetry monitoring in its portable unit and the capability for diagnostic quality blood pressure monitoring in its base unit. Diagnostic quality, as used herein, refers to high-quality data that may be relied upon by professional medical providers for diagnostic and prescriptive patient care, as may be defined by industry and/or regulatory standards such as ANSI/AAMI EC-11, EC-13 and EC-38 for ECG, EC 1099 for $SpO_2$ and ANSI/AAMI SP10 for BP. Distinguished from diagnostic- quality vital signs data are data that are of insufficiently high resolution, integrity or continuity as to render the data informative and thus perhaps useful by medical and industry standards for general patient status monitoring but not useful for real-time diagnostic and prescriptive medicinal practice.

These and additional objects and advantages of the present invention will be more readily understood after consideration of the drawings and the detailed description of the preferred embodiment which follows.

DETAILED DESCRIPTION OF THE PREFERRED EMBODIMENT AND BEST MODE OF CARRYING OUT THE INVENTION

Figure 1:
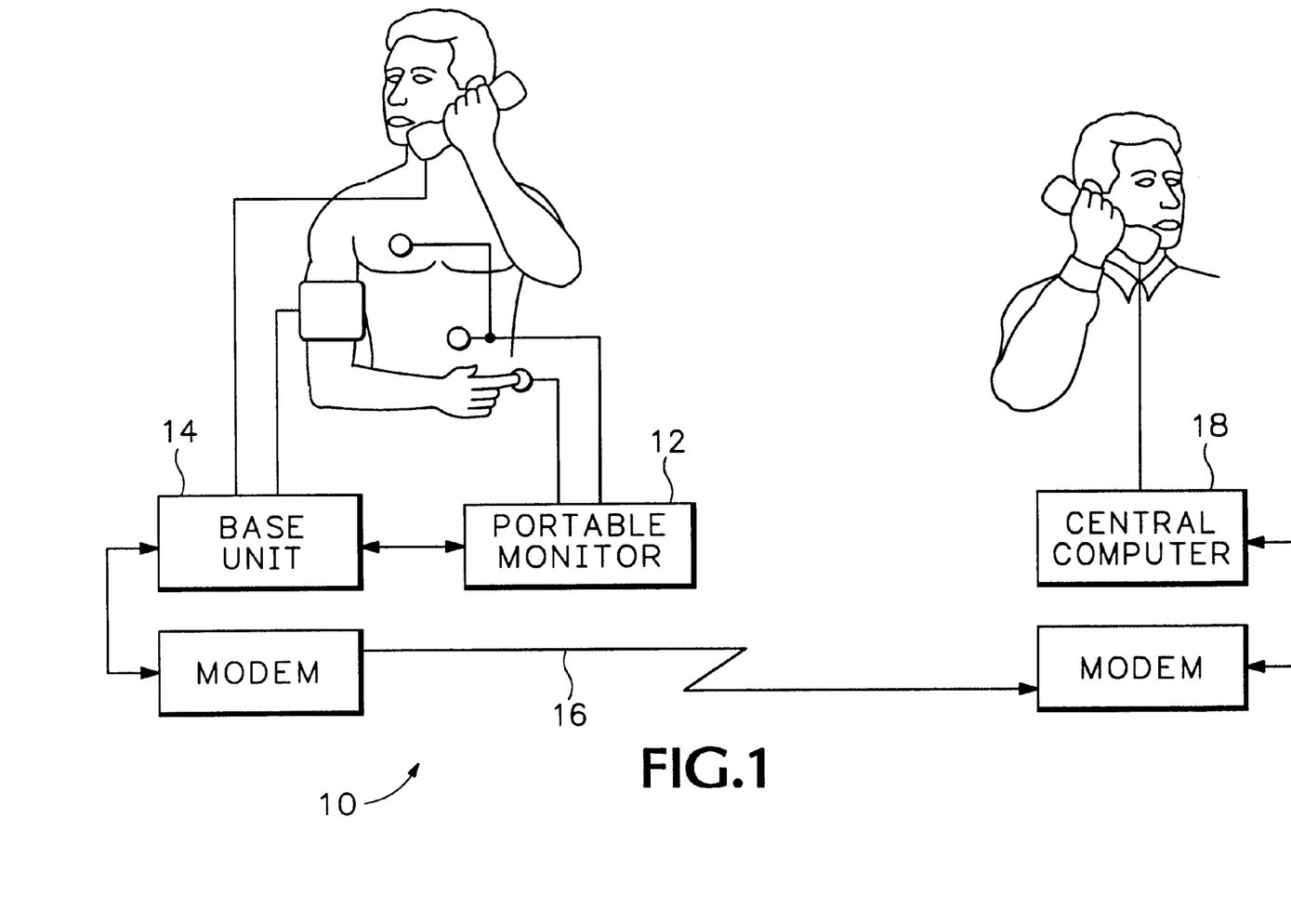
FIG. 1 is a system block diagram of the invented medical patient-monitoring apparatus.

Referring first to FIG. 1, invented apparatus 10 may be seen in the form of a system block diagram to include a portable, lightweight multiple-vital signs monitor 12 docked in a relatively fixed base unit 14. In its preferred embodiment, monitor 12 provides for both twelve-lead ECG and pulse oximetry ($SpO_2$) monitoring of an ambulatory patient indicated in solid outline. Base unit 14 preferably provides for blood pressure monitoring of a seated or reclining patient. Base unit 14 preferably is connected via the public switched telephone network (PSTN) indicated at 16, and two MODEMs, for concurrent voice and data transmission and reception with a central or host computer 18.

Those of skill will appreciate that any plurality of patient vital signs may be monitored in accordance with the invention. Such vital signs may include, for example, electroencephalograph (EEG), ECG, blood-oxygen level, BP, blood-glucose level and blood flow and/or volume, as well as others, may be monitored, and may be communicated to a central computer either in the form of discrete numeric data (as in the case of static $SpO_2$, BP and blood-glucose level data) or continuous waveform data (as in any case wherein relatively short-term aberrations may be important and it is desired to overview relatively raw, continuous data that has not been averaged or otherwise reduced, compacted or interpreted by the patient-connected monitoring equipment, e.g. EEG, ECG, auscultatory, blood-oxygen, plethysmographic, waveform data). Any and all such plural vital signs monitoring and communication of data representative thereof in any suitable form are within the spirit and scope of the invention.

It will be appreciated that communication between portable monitor 12 and base unit 14 may be by radio frequency (RF), infrared or any other suitable wired or wireless communication means, alternative or additional to the mating electrical contact that is provided in accordance with the preferred embodiment of the invention. It will also be appreciated that communication between base unit 14 and central computer 18 (refer to FIG. 1) may be performed by any suitable means including, e.g. cellular, satellite, etc., and in accordance with the teachings of the above-referenced U.S. patent application Ser. No. 08/556,468, now U.S. Pat. No. 5,704,364, or any other suitable communications protocol. Finally, it will be appreciated that portable monitor 12 alternatively may communicate directly with central computer 18, thus bypassing base unit 14, e.g. by the provision of an internal modem within portable monitor 12 and a suitable telephone line jack for PSTN connection, as will be described in more detail below by reference to FIGS. 3 through 7.

Figure 2:
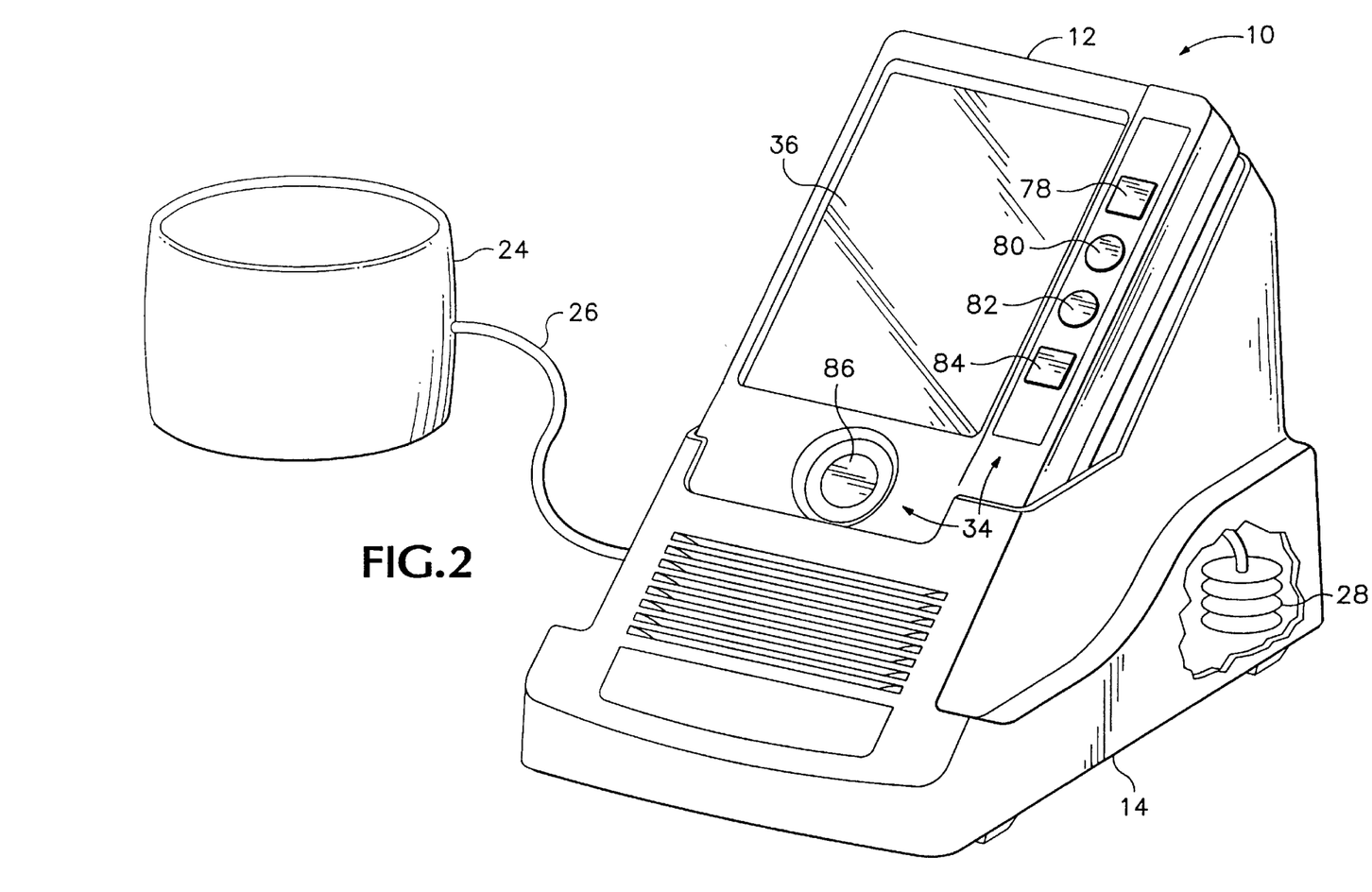
FIG. 2 is an isometric view of the invented monitoring apparatus showing a portable unit docked in a base unit.

FIG. 2 shows how conveniently portable monitor 12 may be docked in base unit 14 for certain vital signs monitoring and vital signs data and voice communication with central computer 18. It will be appreciated that, in accordance with the preferred embodiment of the invention, base unit 14 effectively acts as a speakerphone for voice communication between a patient and a remote health care provider, while also communicating vital signs data to a central site for patient monitoring and diagnosis.

Turning collectively now to FIGS. 3 through 7, portable monitor 12 will be described in detail. Portable monitor 12 may be seen preferably to include a housing 20 and a vital signs monitoring mechanism indicated generally at 22 contained therein. Monitoring mechanism 22 may be seen from FIG. 6 to provide for the tracking of two or more medical patient vital signs, e.g. ECG and blood-oxygen level, in the form of diagnostic quality signal representations stored in a memory device also located preferably within housing 20 and preferably forming a part of monitoring mechanism 22. It will be appreciated that any two or more medical patient vital signs may be monitored, within the spirit and scope of the invention, to produce multiple patient vital signs in the form of diagnostic quality signal representations in accordance with accepted industry or regulatory standards.

In accordance with one important aspect of the invention, portable monitor 12, including its batteries, preferably has an overall weight of less than approximately two pounds (lb) (0.74 kilograms (kg)), more preferably has an overall weight of less than approximately 1 pound (lb) (0.37 kg), and most preferably has an overall weight of less than approximately 15.7 ounces (oz) (0.36 kg), thereby rendering portable monitor 12 extremely lightweight and convenient to use for multiple-vital signs diagnostic medical patient monitoring. Preferably, housing 20 is injection molded from an impact-resistant, lightweight material such as polycarbonate. Reference to FIGS. 3 through 5, 7A and 7B points out another important feature of portable monitor 12: The overall external volume of portable monitor 12, including batteries, preferably is less than approximately 100 cubic inches ($in^3$) (1.63 liters (l)), more preferably is less than approximately 60 $in^3$ (0.975 1l) and most preferably is less than approximately 40 $in^3$ (650 milliliters (ml)). The relatively small volume is achieved by choice of circuit topology, patient interface controls and indicators and I/O ports, while the relatively low weight is achieved by these choices as well as choice of materials, as will be seen.

Portable monitor 12 preferably includes a twelve-lead ECG jack in the form of a printed circuit board (PCB) edge-type connector; a pulse oximetry serial I/O jack; a PCB-type edge connector for base unit input/output (I/O) and portable monitor battery recharging; and a third, expansion port, e.g. a PCMCLA port that may be used for diagnostics and/or equipment maintenance, for direct remote connect via modem or for cellular or local area network (LAN) connection. Although BP electronics and software preferably are in portable monitor 12, the BP I/O port may be seen to be in base unit 14. This is because of the bulk and power requirements of the BP cuff-pressurizing pump motor and because a seated, relaxed patient has been found to be important to BP trend analysis and diagnosis. Of course, those of skill in the art will appreciate that, within the spirit and scope of the invention, the BP pump motor alternatively could be placed within the portable monitor's enclosure.

Referring briefly now to FIG. 2, it is noted from the isometric view of apparatus 10 that portable unit 12 is configured for mating support on and partly within base unit 14. It will be appreciated that in such a mated configuration, portable unit 12 may be recharged by base unit 14 and that other patient vital signs monitoring may be accomplished. For example, in accordance with the preferred embodiment of the invention, BP monitoring may be performed on the patient while the patient is seated, as it is believed that BP monitoring is more accurate when the patient is in relative repose. Base unit 14 thus preferably is equipped with an inflatable BP cuff 24 at the end of an air hose 26 and a base unit-integral pump 28 (shown in FIG. 2 only fragmentarily) operatively connected thereto for inflating and deflating the cuff.

Base unit 14 also preferably may supply power for recharging one or more batteries, e.g. four AA alkaline batteries, within portable monitor 12, and may have an I/O port 30 for supplying signal input and output to and from portable monitor 12. In accordance with the preferred embodiment of the invention, the electronics associated with obtaining diastolic, systolic and mean BP data (as well as pulse data) from BP cuff 24, with temporarily storing such data and with communicating such data to a remote computer in a monitoring and patient care facility is located within portable monitor 12, although it will be appreciated that such electronics may be placed any suitable location within apparatus 10, within the spirit and scope of the invention.

Figure 6:
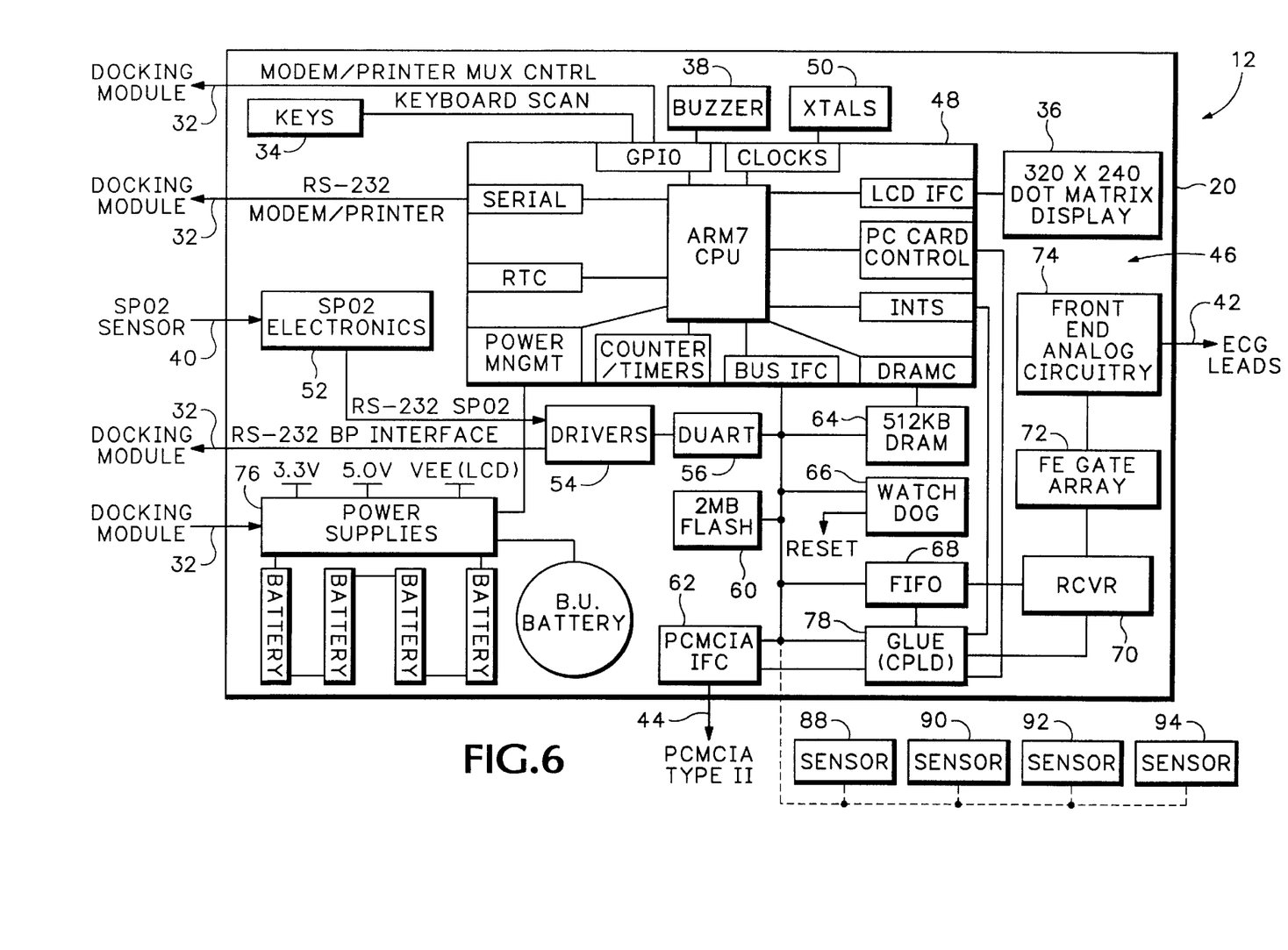
FIG. 6 is a detailed schematic block diagram of the portable unit.
Figure 8:
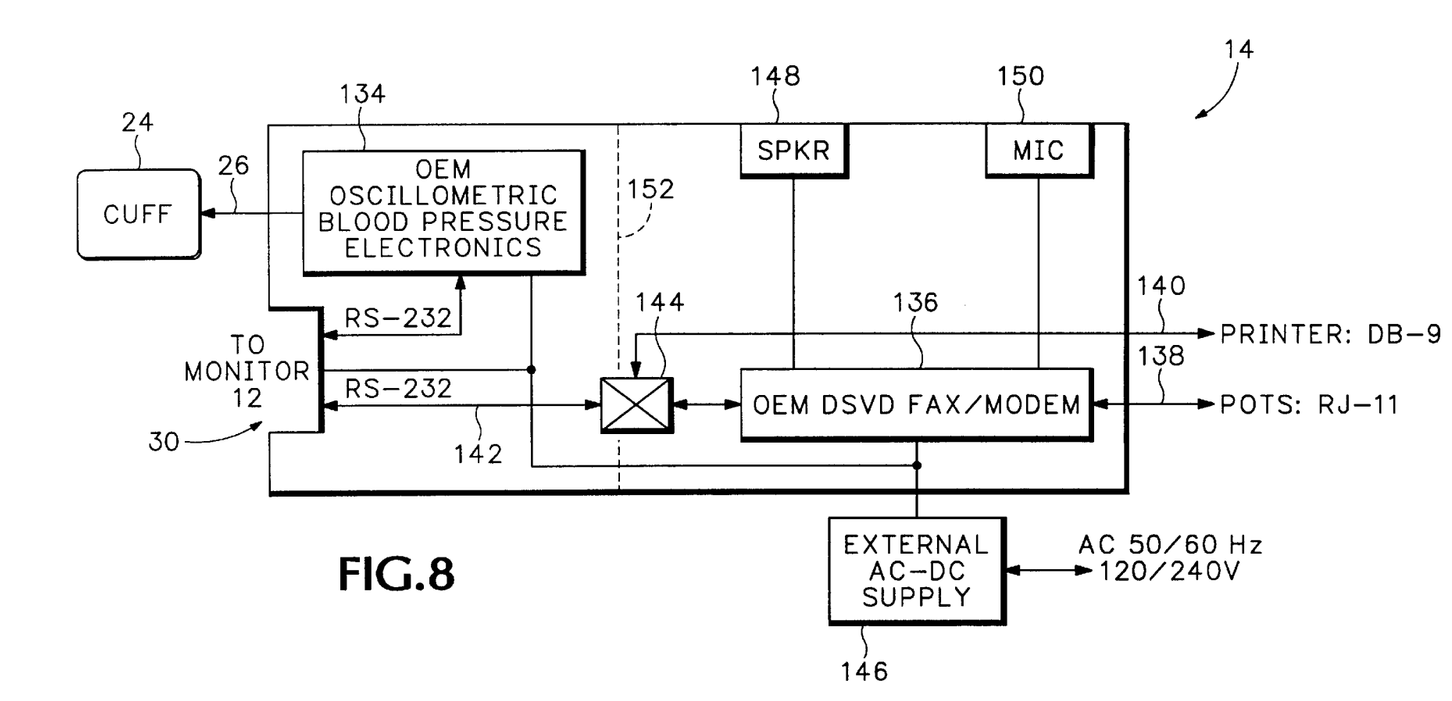
FIG. 8 is a schematic block diagram of the docking module in which the portable unit may be received.

Base unit 14 in its preferred embodiment provides such I/O port 30 via a printed circuit board (PCB) edge connector having a suitable number of finger-like contacts, e.g. thirty, for mating a corresponding I/O port 32 in a base region of portable monitor 12 (refer briefly to FIGS. 6 and 8). Preferably, base unit 14 continuously and automatically trickle charges one or more batteries within portable monitor 12 while the latter is properly docked in the former, thus requiring minimal patient effort. Those of skill will appreciate that such is similar to portable phones, which typically are recharged any time they are properly docked in their AC-coupled home bases. It will also be appreciated that portable monitor 12 is fully functional as a multiple-vital signs monitor even when it is docked in base unit 14. Thus, in accordance with the invention, plural vital signs monitoring may be accomplished while the patient is seated near the base unit, including at least diagnostic-quality ECG, blood oxygen and blood pressure.

Figure 3:
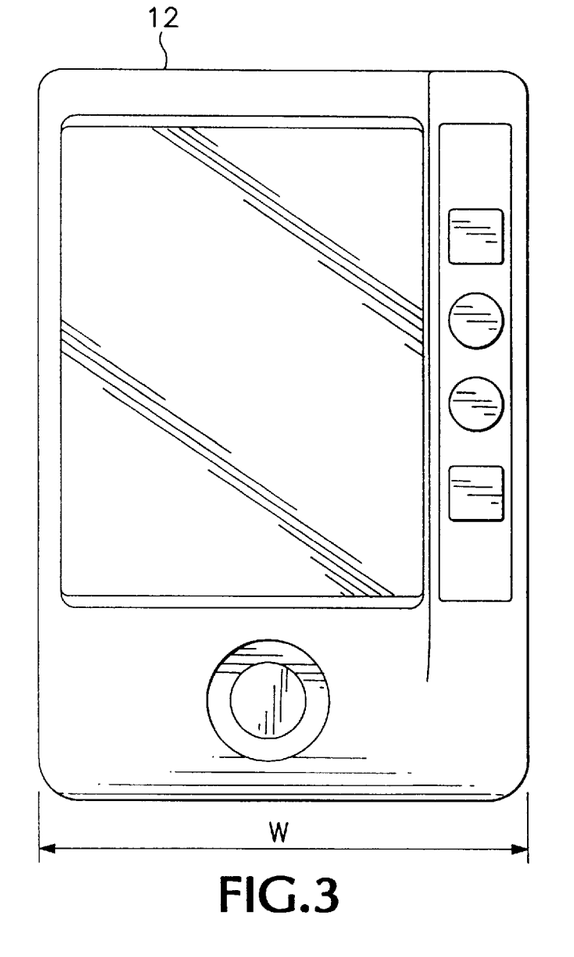
FIG. 3 is a front elevation of the portable unit illustrating its overall dimensions and features.
Figure 4:
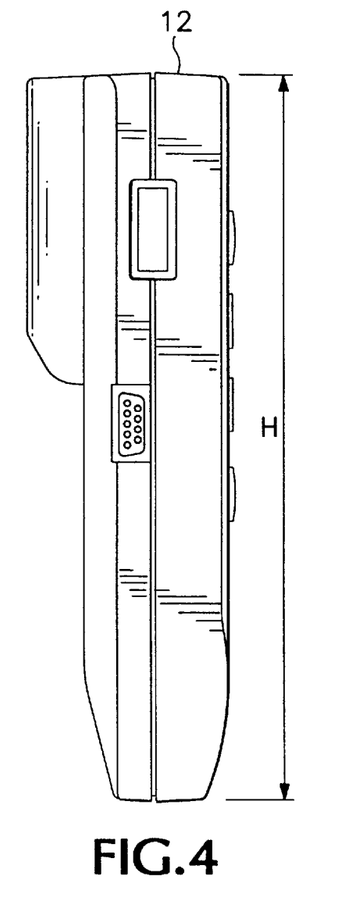
FIG. 4 is side elevation of the portable unit showing its overall dimensions and features.
Figure 5:
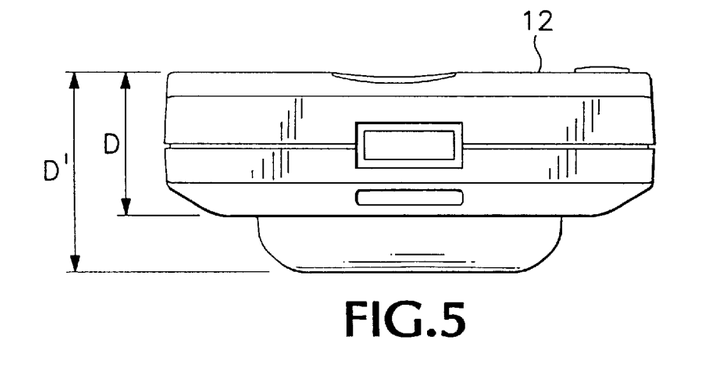
FIG. 5 is an end elevation of the portable unit showing its overall dimensions and features.

Referring now to FIGS. 3 through 5, portable monitor 12 may be seen, respectively, in front, side and end elevations. These elevations of portable monitor 12 illustrate the compactness of portable monitor 12 as well as its low-mass versatility in providing convenient, portable, multiple patient vital signs monitoring. It may be seen that portable monitor 12, in accordance with a preferred embodiment of the invention, is a right parallelepiped measuring approximately 6.18" (15.7 cm) in height H, 4.14" (10.5 cm) in width W and 1.2" (3.05 cm) in depth D except in a rear battery pack region where monitor 12 measures approximately 1.68" (4.27 cm) in depth D'. The sleek design renders portable monitor 12 readily grasped in the patient's hand, and easily slipped into a shirt, blouse, pants or robe pocket for ambulatory use or a provided carrying case.

It will be appreciated from FIGS. 2 through 5 that portable monitor 12 is smoothly rounded at its corners and edges, and has an overall aesthetic appeal. Moreover, it may be seen that the I/O ports to which cables are connected when monitor 12 is in use are conveniently located on edge surfaces of the monitor's housing, whereas the display and pushbuttons including the prominent RECORD button are conveniently located on the front surface of the housing, rendering the portable monitor easy to use during an ambulatory monitoring and diagnostic session. Because of its modest size, modular construction, the architecture of the electronic circuitry therein and the choice of materials used in its fabrication and assembly, monitor 12 weighs in at just under one pound, making it a featherweight compared to prior art multiple vital signs monitors. This high functional density in a multiple vital signs monitor—wherein functionality is relatively high but size and mass are relatively low—is one of the key advantages of the invention.

Referring next briefly to FIG. 6, a detailed schematic block diagram of portable monitor 12 illustrates the circuit and functional partitioning that renders possible the production of an extremely low-mass multiple vital signs monitor. Portable monitor 12 preferably includes a keyboard preferably in the form of a set of pushbutton switches 34, a dot matrix display 36, an annunciator preferably in the form of a buzzer or beeper 38, various I/O ports such as a pulse oximetry data serial port 40, a multi-lead ECG port 42, a PCMCIA or PC-Card port 44, a docking module I/O port 32 and power supply-powered electronic circuitry 46 within integral housing 20 indicated in rectangular outline. Electronic circuitry 46 is illustrated schematically and will be described in some detail in mediately below.

Electronic circuitry, or electronics, 46 preferably includes a microprocessor ("CIRRUS 7110") 48 and associated crystals ("XTALS") 50; an SpO$_2$ device or unit ("SPO2 ELECTRONICS") 52, e.g. the OEM device made by Nonin; RS-232 I/O port driver/receiver circuitry ("DRIVERS") 54; a dual universal asynchronous receiver/transmitter ("DUART") 56; a 2 megabyte (MB) flash memory 60; a PCMCIA interface ("IFC") 62; a 512 kB dynamic read-and-write memory (DRAM) 64; a watchdog timer ("WATCHDOG") 66; a first-in/first-out (FIFO) memory 68 for pacing the asynchronous, continuous ECG waveform data samples; an ECG receiver ("RCVR") circuit 70; an ECG, field-effect (FE) gate array 72; ECG front-end analogue circuitry 74; power supplies 76; and miscellaneous so-called 'glue' circuitry 78, e.g., in the form of a complex programmable logic device ("CPLD").

Microprocessor 48 preferably integrally includes a central processing unit ("ARM7 CPU"), clocks, a general-purpose I/0 interface (GPIO), a serial port ("SERIAL"), a real-time clock (RTC), power management circuitry ("POWER MNGMT"), various counters/timers, an I/O bus interface ("BUS IFC"), a DRAM controller ("DRAMC"); interrupt control circuitry ("INTS"), PC-Card control and an LCD interface ("LCD IFC") such as that found in a Cirrus 7110 processor. Housing-integral power supplies 76 preferably provide a rechargeable bank of four standard, series-connected AA alkaline batteries—as well as a backup ("B.U.") lithium battery that powers essential functions such as the RTC when one or more of the alkaline batteries is being replaced—and appropriate regulation circuitry for all of the electronics and other I/O devices housed within portable monitor 12.

Preferably, two different types of batteries form a part of power supplies 76. Preferably, a first type of battery, e.g. alkaline, provides for the relatively high-current, short-life, requirements of portable monitor 12 and a second type of battery, e.g. lithium, provides for the relatively low-current, long-life, requirements thereof. For example, the chosen battery type, mix and number preferably may provide portable monitor 12 with the capacity to perform constant monitoring and periodic, e.g. on-demand, reporting for at least twenty-four hours as well as active, e.g. on-demand, monitoring and reporting for up to two weeks, both without needing recharging. Thus, it will be appreciated that power supplies 76 provide portable monitor 12 extended operation independent from base unit 14 in accordance with the preferred embodiment of the invention.

It is noted that the four AA alkaline batteries weigh approximately 3.4 oz (0.078 kg) total, so it will be appreciated that the alkaline batteries presently contribute significantly (more than 20%) to the overall weight of portable monitor 12. It is contemplated, then, that by the use of alternative battery cell types, e.g. a lithium ion or similar high-current, long-life disk battery, the weight of the batteries and thus of portable monitor 12 may be further reduced, within the spirit and scope of the invention. Similarly, it is contemplated that the volume of such high-current, long-life batteries may be reduced commensurately with their mass, also within the spirit and scope of the invention, thereby further increasing the functional density of the invented apparatus. Nevertheless, even with the preferred AA alkaline battery design represented in the preferred embodiment of the invention, the housing and monitoring mechanism which includes the power supplies' batteries integrally contained therein weighs a mere 15.7 oz, providing remarkable high functional density in a multiple vital signs monitor.

Referring briefly to FIG. 2, the human interface between portable monitor electronics 46 and the medical patient or other user thereof thus will be understood to include keyboard 34 preferably including plural, e.g. five, pushbutton switches 78, 80, 82, 84, 86 including the prominent RECORD switch 86 centered in the lower front surface of the housing; display 36 which preferably may be a 320×240 reflective dot matrix monochrome display having a (0.3 mm) 12 mil dot pitch, thus enabling AAMI monitoring resolution requirements for at least three leads of simultaneous, real-time ECG or EEG or other continuous, high-resolution waveform data; and buzzer or beeper 38. Firmware resident within flash memory for at least three leads of simultaneous, real-time ECG or EEG or other continuous, high 60—in cooperation with the ARM7 CPU, the DRAMC and the GPIO—polls the keyboard, updates the display and signals the buzzer to communicate with the patient before, during and after an ambulatory or stationary monitoring session.

Referring again now to FIG. 6, it will be appreciated that most of the cooperative components are stock, rather than custom, chips or integrated circuits (ICs) and circuit modules that are readily available from various manufacturers and mounted, very simply, on a singular multi-layer PCB (not shown in FIG. 6, but shown in FIG. 7B to be described below). Yet the architecture of electronics 46 renders the electronic circuitry and hardware within portable monitor 12 straightforward and relatively inexpensive to manufacture and maintain while providing great versatility in multiple patient vital signs monitoring. Importantly, the architecture represents a desirable tradeoff between processing power on the one hand and power consumption and cost—including hardware and firmware development costs and assembled and tested monitor costs—on the other.

Exemplary of the way in which development and recurring costs are minimized are the stability and support available from the manufacturers of some of the stock components described above. The Cirrus 7110 processor is a mature OEM product characterized by a low-power requirement and high-powered support including software simulation and development system and operating system support. Similarly, SpO$_2$ electronics device 52 manufactured by Nonin is a mature OEM product characterized by a straightforward, relatively low-speed serial interface in the form of a hybrid circuit module that is easily plugged into a motherboard. Similarly, the ECG RCVR circuit 70 and FE gate array 72, manufactured by Mortara are mature, off-the-shelf modules and components that are easily interfaced with and integrated into a PCB or motherboard. Finally, it will be appreciated that PCMCIA interface 62 manufactured by a wide variety of manufacturers-an interface that is now nearly ubiquitous in connection with personal computers (PCs)—is a very mature and versatile product from the standpoint of ease of manufacture, use and maintenance.

Indeed, the provision of a PCMCIA interface, or PC-Card, in a portable multiple vital signs monitor creates a plethora of additional features. Standard applications of PCMCIA in the PC industry may be imported to the invented vital signs monitor, including use of it as extended flash (electronic) or rotating (magnetic or optical) memory or other mass storage medium, a local area network (LAN) connection, a digital cellular wireless communications interface, a SCSI interface, a modem with phone jack, a data acquisition card, a high-speed parallel interface or the like.

Those of skill in the art will appreciate also that wireless transtelephonic multiple vital signs data communication capability may be provided to the portable monitor by way of an integral modular controller interface, e.g. a PCMCIA having an oscillator, a modulator and a suitable speaker. In accordance with the preferred embodiment of the invention, the PCMCIA may be used as the interface through which flash memory is loaded with production firmware, through which firmware updates are made and through which diagnostics and troubleshooting are performed during manufacture and field servicing of the portable monitor. Myriad other applications are possible, and all are within the spirit and scope of the invention.

Briefly, the firmware resident within flash memory 60, in accordance with the preferred embodiment of the invention, controls the I/O ports, manages memory allocation including the buffers within DRAM 64 in the well-known looping memory manner by which only recent waveform data of interest is accessible for diagnostic purposes and older data not of interest is recorded over, handles communication with docking unit 14 or an optional, external printer or other data communications equipment (DCE) or data terminal equipment (DTE), polls the keyboard by debouncing the switches and detecting closures, updates the dot matrix display and minimizes power consumption without loss of vital data.

Those skilled in the art will appreciate how straightforwardly BP, blood oxygen level, ECG, pacemaker or defibrillator pulses, EEG and other vital signs represented by analogue signals may be filtered, pacemaker pulses may be detected, characteristic complexes may be sampled, as by over-sampling plural samples, optionally averaging the plural samples and decimating the samples to produce for storing or recording in a memory device digitized representations of an ECG or EEG waveform of diagnostic quality in memory for later outplay. It will be appreciated that decimation is used in its broadest sense to refer to a process whereby only a pertinent periodic portion, or fraction, of a sampled vital sign is used in vital signs monitoring. Recorded samples may be stored in so-called looping memory such that only pertinent data around a significant trigger event consumes memory. Recorded samples may be time-stamped, using the RTC, in order to render waveform data meaningful even in the event of a temporary data dropout or other interruption, thus avoiding misinterpretation of fragmented vital signs data.

Such may be done, for example, in accordance with the teachings of commonly owned U.S. Pat. No. 4,958,641 entitled HEART DATA MONITORING METHOD AND APPARATUS issued Sep. 25, 1990; U.S. Pat. No. 4,977,899 entitled HEART DATA MONITORING METHOD AND APPARATUS issued Dec. 18, 1990; U.S. Pat. No. 5,012,814 entitled IMPLANTABLE-DEFIBRILLATOR PULSE DETECTION-TRIGGERED ECG MONITORING METHOD AND APPARATUS issued May 7, 1991; U.S. Pat. No. 5,128,552 entitled SYSTEM AND METHOD FOR POWER SUPPLY PRESERVATION IN A PERSONAL HEALTH MONITOR issued Jul. 7, 1992; U.S. Pat. No. 5,317,269 entitled WRIST-WORN ECG MONITOR WITH BATTERY END OF LIFE PREDICTION issued May 31, 1994; U.S. Pat. No. 5,351,695 entitled WRIST-WORN ECG MONITOR issued Oct. 4, 1994; and U.S. Pat. No. 5,613,495 entitled HIGH FUNCTIONAL DENSITY CARDIAC MONITORING SYSTEM FOR CAPTURED WINDOWED ECG DATA issued Mar. 25, 1997, the disclosures of which are incorporated herein by this reference.

FIG. 6 shows in schematic block diagram form and in phantom connection with the BUS IFC some of the vital signs sensors that may be incorporated into apparatus 10, within the spirit and scope of the invention. For example, plethysmographic data may be sampled and recorded via a plethysmographic sensor 88; auscultatory data may be sampled and recorded via an auscultatory sensor 90; blood-glucose level data may be sampled and recorded via a blood-glucose level sensor 92; electroencephalographic (EEG) data may be sampled and recorded via an EEG sensor 94; etc. in addition to or instead of the sampling and recording of ECG, blood-oxygen level and BP data as described and illustrated herein with respect to the preferred embodiment of the invention. Those of skill in the arts will appreciate that any two or more vital signs concurrently may be monitored, recorded and outplayed either locally or remotely for oversight by medical personnel for diagnostic purposes, all within the spirit and scope of the invention.

Figure 7A:
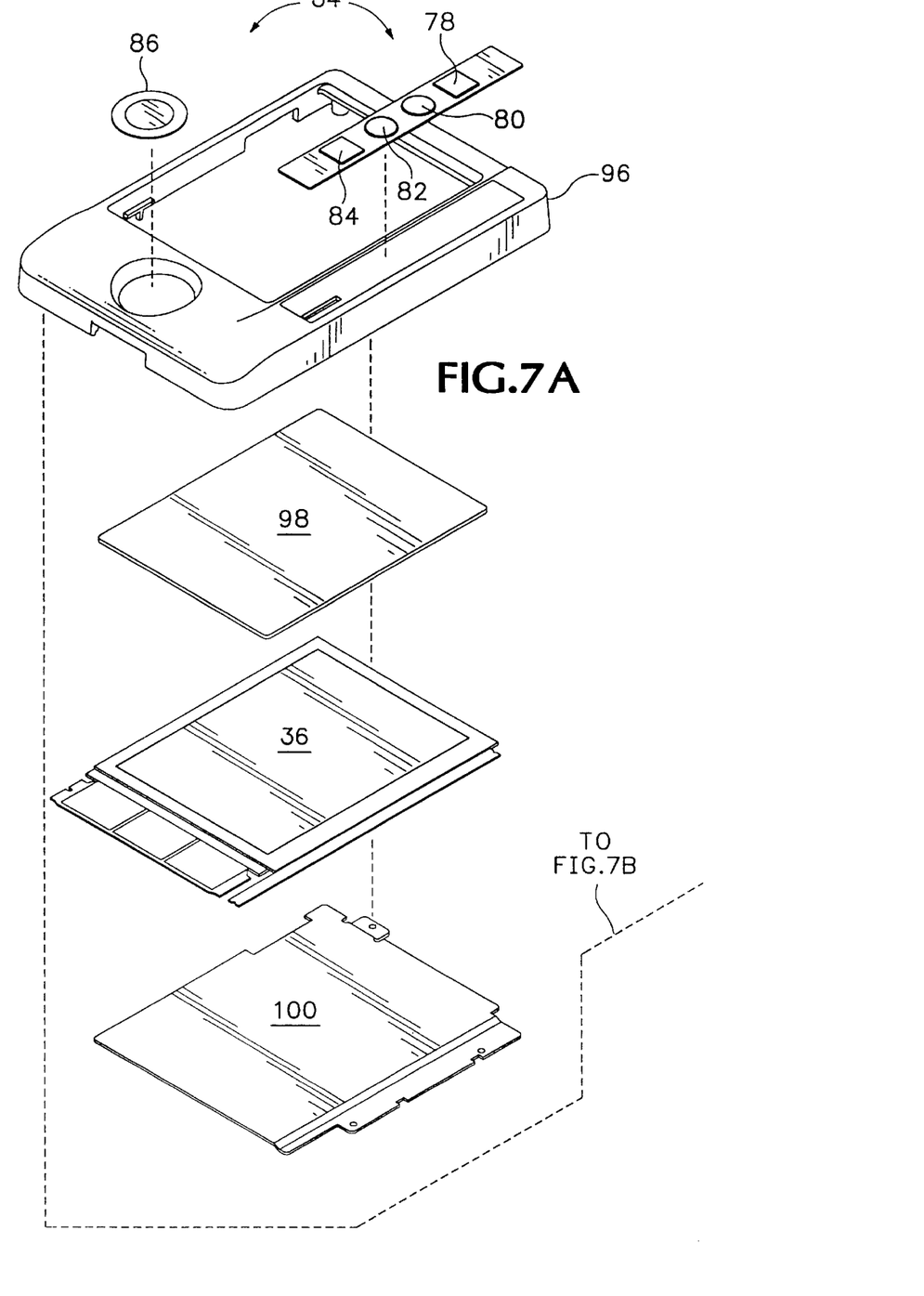
FIGS. 7A and 7B represent an exploded assembly drawing of the portable unit showing its component parts and how they fit together.
Figure 7B:
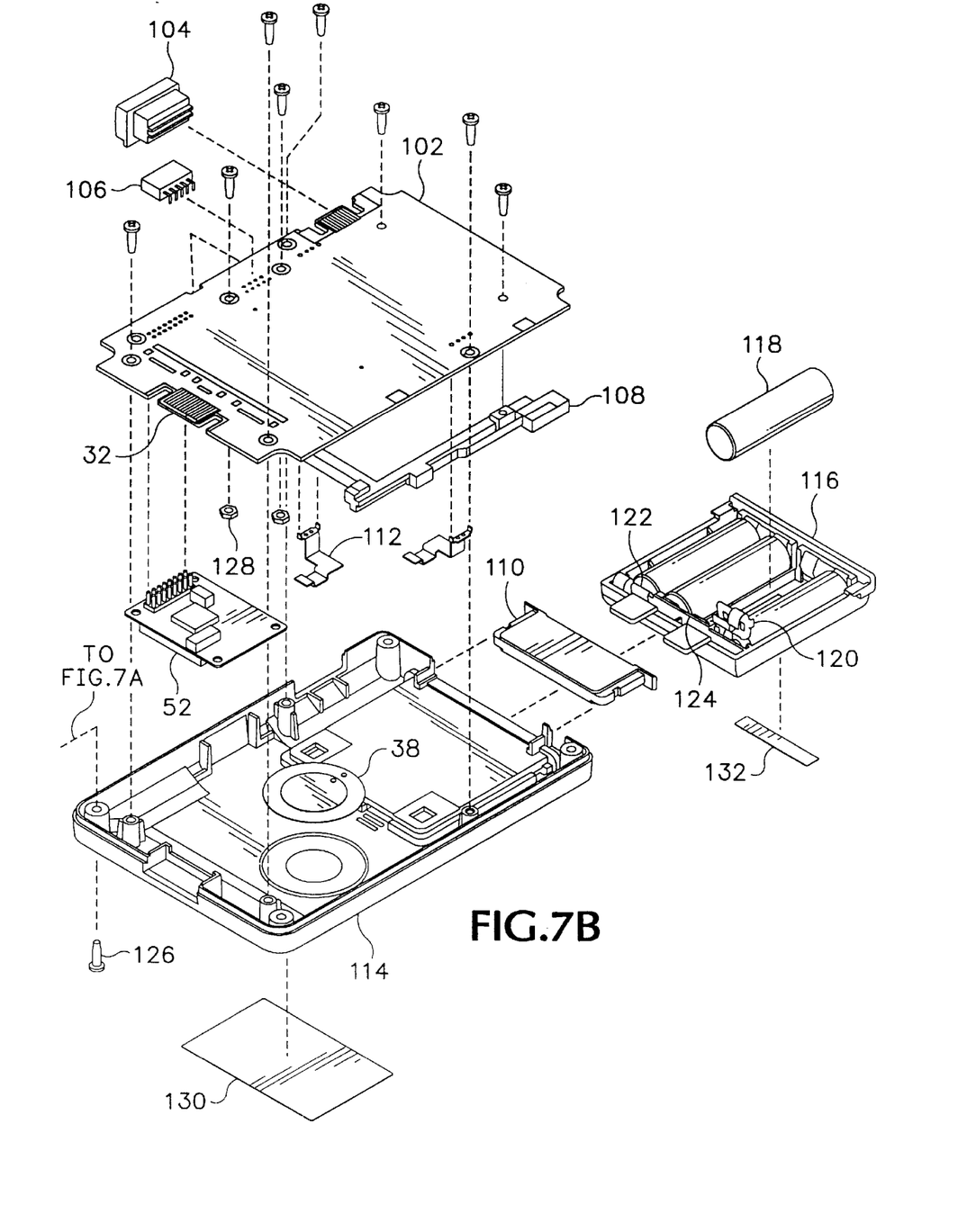

Referring now to FIGS. 7A and 7B, it may be seen how the component parts of invented portable monitor 12—which forms part of invented apparatus 10—fit together, by way of an exploded assembly drawing of the portable monitor. FIG. 7A shows portable monitor components including a top case or molded face plate 96; menu pushbuttons 78, 80, 82, 84 and RECORD pushbutton 86 that make up keyboard 34 liquid crystal display; and LCD window 98, which collectively may be seen to form the front half of housing 20. Below display window 98 is LCD 36 and below that is an LCD bracket 100. It will be appreciated that the components shown in FIG. 7A all fit snugly together, with microstrip pushbuttons 78, 80, 82, 84 and discrete pushbutton 86 fitting within recesses formed in the front surface of face plate 96 and with LCD 36, window 98 and bracket 100 fitting within a recess formed in the rear surface thereof.

FIG. 7B shows a printed circuit board PCB 102 with PC edge connector or base unit I/O port 32, twelve-lead ECG connector shroud 104 that forms a part of ECG port 42 and a right-angle DB9 female connector 106 that forms a part of $SpO_2$ serial port 40. Visible therebeneath for PCB 102 mounting is a PCMCIA surface-mount technology (SMT) connector 108 and a corresponding PCMCIA plug-in cover 110. Also visible therebeneath are dual power contacts such as contact 112 for connecting piezoelectric buzzer 38 and the alkaline batteries with the circuitry of PCB 102. Also visible therebeneath is $SPO_2$ unit 52 for piggy-backed mounting and connection to PCB 102. Therebeneath is a bottom case or molded back plate 114 and laterally spaced therefrom is an alkaline battery module 116 for holding four AA alkaline batteries such as battery 118 and for supplying power therefrom to circuitry on PCB 102 via various positive, negative and inter-battery contacts 120, 122, 124.

Referring collectively to FIGS. 7A and 7B, it may be seen that nine screws such as screw 126 and two locknuts with washers such as locknut 128 secure various components together with a minimum of hardware. Finally, it may be seen that one or more product labels such as labels 130, 132 may be affixed to portable monitor 12, as indicated. It will be appreciated that certain details of construction are omitted in FIG. 7B for the sake of clarity. Discrete electrical components such as crystals, decoupling capacitors, resistors, test pins, etc. mounted on PCB 102 are not shown, nor are the signal traces in the multiple layers of the PCB.

PCB fabrication and circuit design may be accomplished in any suitable manner consistent with low mass and electromechanical integrity. It will be appreciated that, in accordance with the preferred embodiment of the invention, hardware and component counts are minimized to lower cost, to facilitate assembly and to reduce weight. It will also be appreciated that circuit and device emissions preferably are minimized by circuit design and PCB routing and layup (e.g. by the use of thin layers and integral power and ground distribution planes) techniques that do not add weight. The highest scale circuit integration is preferred to minimize component count, the lowest power devices are chosen, e.g. CMOS devices that will work at 3.3V and only essential circuitry is powered, all in order to minimize power consumption and to reduce the power supplies' battery weight. Connector weight is minimized by using, wherever possible, printed circuit edge connectors requiring little or no on-board hardware. Importantly, the battery module is rendered easily reconfigured by its snap-fit, 'outboard' design, thereby providing an upgrade path to different and preferably lower-mass battery types as such become available.

Referring finally to FIG. 8, and for the sake of completeness, a schematic block diagram of docking module 14 illustrates the functional blocks that enable the docking module to communicate with portable monitor 12 via an RS-232 I/O port and with a remote host computer (not shown, but of conventional design and providing for bi-directional, simultaneous voice and data communication between the monitored patient and a medical technician) via a PSTN communication port.

Base or docking module 14 preferably includes a oscillometric BP electronics 134 (including pump 28 of FIG. 2 not shown) and associated cuff air hose 26 for connection with air inlet/outlet port on inflatable BP cuff 24; an RS-232 I/O port 30 for operative communication with portable monitor 12; an OEM V.34 digital simultaneous voice/data (DSVD) fax/modem circuit 136 and associated PSTN I/O port 138; an RS-232 DB9 printer I/0 port 140; a printer/DSVD control line 142 from portable monitor 12 and an associated logic switch 144 controlled thereby to select whether monitor 12 is in communication with an external printer or the PSTN; an external, so-called power 'brick', or AC/DC power supply 146; a speaker ("SPKR") 148; and a microphone ("MIC") 150. Preferably, and as indicated by a broad, vertical dashed line, a patient-isolation barrier 152 is provided within docking module 14 to meet regulatory requirements that a patient who may be connected to portable monitor 12 be safely isolated from the PSTN.

It will be appreciated that alternative circuitry, or circuitry alternatively configured and/or partitioned, may within the spirit and scope of the invention be provided within docking module 14 to provide different and/or additional patient multiple vital monitoring capability. It will also be appreciated that the functional capability provided by invented apparatus 10 may be differently partitioned between portable monitor 12 and its associated docking module 14, all within the spirit and scope of the invention.

METHOD OF USE OF THE INVENTED DEVICE

It may be seen, then, that the invented monitoring system including the portable monitor received in a relatively fixed base is used to monitor or track a medical patient's vital signs and to communicate such vital signs in real time to a remote site for diagnostic and prescriptive purposes, i.e. with a minimum delay on the order of a second or less between the sample or measurement and the receipt thereof at the remote site. Preferably, such is done conveniently over a single switched telephone line or wireless link such as a digital cellular satellite link such that little or no extra equipment is required at the patient's site, which typically is the patient's home. Preferably, two-way voice communication also is provided between the patient being monitored in real time and the remote physician or care provider. Yet the base and portable monitor that collectively are referred to herein as the monitoring system each are small, lightweight and low-mass, and are easily and inexpensively manufactured and maintained.

Accordingly, while the present invention has been shown and described with reference to the foregoing preferred apparatus, it will be apparent to those skilled in the art that other changes in form and detail may be made therein without departing from the spirit and scope of the invention as defined in the appended claims.

We claim:

1. A portable, lightweight, multiple-vital signs diagnostic medical patient monitor comprising;

a housing and a vital signs monitoring mechanism contained within said housing, said mechanism providing for the tracking of two or more medical patient vital signs in the form of diagnostic quality signal representations, said housing and said monitoring mechanism collectively having an overall weight of less than approximately 2 pounds, wherein one of the two or more patient vital signs is an electrocardiogram (ECG) and wherein said housing includes one or more external ports for connecting ECG cables to said monitoring mechanism thereby to provide for concurrent tracking of up to twelve-lead ECG vital signs and at least one other of patient vital signs.

2. The monitor of claim 1, wherein one of said at least one other of patient vital signs, the monitoring of which is provided by said monitoring mechanism, includes a medical patient's blood-oxygen level.

3. The monitor of claim 1, wherein one of said at least one other of patient vital signs, the monitoring of which is provided by said monitoring mechanism, includes a medical patient's blood pressure.

4. The monitor of claim 1, wherein one of said at least one other of patient vital signs, the monitoring of which is provided by said monitoring mechanism, includes a medical patient's blood-glucose level.

5. The monitor of claim 1, wherein one of said at least one other of patient vital signs, the monitoring of which is provided by said monitoring mechanism, includes a medical patient's electroencephalogram (EEG).

6. The monitor of claim 1, wherein one of said at least one other of patient vital signs, the monitoring of which is provided by said monitoring system, includes a medical patient's blood flow level.

7. The monitor of claim 1, wherein said monitoring mechanism includes an integral modular controller interface for operative connection with an external device.

8. A portable, lightweight, multiple-vital signs diagnostic medical patient monitor comprising;

a housing and a vital signs monitoring mechanism contained within said housing, said mechanism providing for the tracking of two or more medical patient vital signs in the form of diagnostic quality signal representations, said housing and said monitoring mechanism collectively having an overall weight of less than approximately 2 pounds, wherein said monitoring mechanism includes a memory device and an integral decimator for sampling and averaging plural samples of a patient vital sign to produce stored averages for recording in the memory device.

9. A portable, lightweight, multiple-vital signs diagnostic medical patient monitoring system, comprising;

a monitor including a vital signs monitoring mechanism providing for the tracking of two or more medical patient vital signs in the form of signal representations, said monitor having a housing, a power supply and an overall weight of less than approximately 2 pounds; and a base in communication with a remote practitioner via a communication line and adapted to receive the monitor to establish communication between the monitor and the practitioner, wherein the system provides a device for the tracking of two or more medical patient vital signs in the form of diagnostic quality signal representations.

10. The system of claim 9, wherein the monitor has an overall weight of less than approximately 1 pound.

11. The system of claim 10, wherein the monitor has an overall volume of less than approximately 60 cubic inches.

12. The system of claim 10, wherein the monitor has an overall volume of less than approximately 40 cubic inches.

13. The system of claim 10, wherein one of the two or more medical patient vital signs is an electrocardiogram (ECG), and wherein said monitor includes one or more external ports for connecting twelve-lead ECG cables to said monitoring mechanism which provides for concurrent tracking of up to twelve-lead ECG vital signs and at least one other patient vital signs.

14. The system of claim 9, wherein the system includes means for enabling concurrent transfer of the signal representations and at least one way voice communication over the single communication line.

15. The system of claim 14, wherein the monitor includes a timer and wherein the signal representations are time-stamped to indicate the time of day when the represented vital signs were monitored.

16. The system of claim 9, wherein one of the two or more patient vital signs includes a medical patient's blood pressure.

17. The system of claim 16, wherein said base includes blood pressure sensing electronics and a blood pressure cuff.

18. The system of claim 9, wherein one of the two or more patient vital signs, the monitoring of which is provided by said monitor, includes a medical patient's blood-oxygen level.

19. The system of claim 9, wherein one of the two or more patient vital signs, the monitoring of which is provided by said monitor, includes a medical patient's blood-glucose level.

20. The system of claim 9, wherein one of the two or more patient vital signs, the monitoring of which is provided by said monitor, includes a medical patient's electroencephalogram (EEG).

21. The system of claim 9, wherein one of the two or more patient vital signs, the monitoring of which is provided by said monitor, includes a medical patient's blood flow level.

22. The system of claim 9, wherein said monitor includes an integral modular controller interface for operative connection with an external device.

23. The system of claim 9, wherein said monitor includes a memory device and an integral decimator for sampling and averaging plural samples of a patient vital sign to produce stored averages for recording in the memory device.

* * * * *

UNITED STATES PATENT AND TRADEMARK OFFICE
CERTIFICATE OF CORRECTION

PATENT NO. : 5,931,791
DATED : August 3, 1999
INVENTOR(S) : Sabri et al.

It is certified that error appears in the above-indentified patent and that said Letters Patent is hereby corrected as shown below:

Column 1, line 40, "talking" should be --taking--.

Column 2, line 6, "fill-function" should be --full-function--.

Column 2, line 21, "EC 1099" should be --IEC 1099--.

Signed and Sealed this

Tenth Day of April, 2001

Attest:

NICHOLAS P. GODICI

Attesting Officer     Acting Director of the United States Patent and Trademark Office